United States Patent [19]

Little, III et al.

[11] Patent Number: 4,494,551
[45] Date of Patent: Jan. 22, 1985

[54] ALTERABLE FREQUENCY RESPONSE ELECTROCARDIOGRAPHIC AMPLIFIER

[75] Inventors: Charles A. Little, III, Palm Bay; Raymond B. Patterson, III, Melbourne, both of Fla.

[73] Assignee: Medicomp, Inc., Melbourne, Fla.

[21] Appl. No.: 441,175

[22] Filed: Nov. 12, 1982

[51] Int. Cl.³ .................................................. A61B 5/04
[52] U.S. Cl. ...................................... 128/696; 128/901; 128/902; 330/85; 328/167; 364/415
[58] Field of Search .................. 330/107, 85; 328/167; 364/415, 417, 605; 128/663, 673-675, 733, 696, 698, 700, 702, 706, 900-902

[56] References Cited

U.S. PATENT DOCUMENTS

| | | | |
|---|---|---|---|
| 3,087,488 | 4/1963 | Streimer | 128/900 |
| 3,534,282 | 10/1970 | Day . | |
| 3,569,852 | 3/1971 | Berkovits | 128/696 |
| 3,579,138 | 5/1971 | Harris et al. | 128/902 |
| 3,581,219 | 5/1971 | Alexander | 128/902 |
| 3,667,055 | 5/1972 | Uchida | 330/85 |
| 4,161,945 | 7/1979 | Grossman . | |
| 4,213,467 | 7/1980 | Stulen et al. | 128/733 |
| 4,227,155 | 10/1980 | Lerma | 330/85 |
| 4,261,369 | 4/1981 | Allor . | |
| 4,322,641 | 3/1982 | Packard | 330/107 |
| 4,323,798 | 4/1982 | Watkins | 330/107 |
| 4,331,158 | 5/1982 | Partridge . | |

OTHER PUBLICATIONS

Duffin et al., "A 24 Channel Electrocardiograph Preamplifier" *Proceedings 23rd ACEMB*-Washington Hilton Hotel, Wash. DC, Nov. 15-19, 1970, p. 193.

*Primary Examiner*—William E. Kamm
*Assistant Examiner*—Mitchell J. Shein
*Attorney, Agent, or Firm*—Barnes & Thornburg

[57] ABSTRACT

An electrocardiographic amplifier having an integrator in the feedback loop between the amplifier's input and output whose time constant is varied by the duty cycle of a series switch to vary the low frequency 3 dB roll-off point as a function of the detected low frequency noise in the amplifier output signal. A capacitor is switched in parallel with the inverting feedback resistor to lower the high frequency 3 dB roll-off point in response to detected high frequency noise.

7 Claims, 3 Drawing Figures

DUTY CYCLE = $\frac{t_{ON}}{T}$

ALTERABLE FREQUENCY RESPONSE ELECTROCARDIOGRAPHIC AMPLIFIER

BACKGROUND OF THE INVENTION

The present invention relates generally to amplifiers and, more specifically, to an improved amplifier for use in electrocardiographic monitoring equipment.

Electrocardiographic monitoring apparatus generally includes a plurality of electrodes appropriately placed on a patient which transmits ECG signals to an amplifier which are amplified and recorded typically on a strip chart or stored in a memory. The input signal represents the ECG signal as well as noise. Often the presence of a noise does not seriously impair the usefulness of the ECG data, however, noise may saturate the input amplifier and, thus, cause loss of data when the output signal is locked at a fixed value and it takes a finite time for the amplifier to come out of saturation.

One approach for alleviating this problem is to use a narrow bandwidth amplifier. The prior art has generally limited the bandwidth from 1 Hz to 30 Hz. Such a limitation drastically reduces the quality of the signal received and does not provide adequate analysis of the QRS shape, the ST rise and the R-R interval. An effort to remove 60 cycle noise is illustrated in U.S. Pat. No. 4,161,945, to Grossman, wherein a notch filter is inserted between the preamplifier and the power amplifier to remove the 60 cycle signal once it is detected. The control circuit will remove the notch filter when 60 cycle noise is not present.

In the prevention of the transmission of transients, for example, the pacemaker spikes or electrode switching is attenuated in the prior art by forming an integrator or muting stage between the preamplifier and the power amplifier as specifically shown in U.S. Pat. Nos. 3,534,282, to Day and 4,331,158, to Partridge. Manual adjustments of high pass filter, low pass filter and amplifier gain has been provided as illustrated in U.S. Pat. No. 4,261,369, to Allor.

The adjustment of the low frequency 3 dB roll-off point from 0.05 Hz to 1.0 Hz in response to a predetermined level of low frequency noise and the lowering of the upper frequency 3 dB roll-off point from 50 Hz to 10 Hz in response to high frequency noise is specifically described in U.S. Pat. No. 3,569,852, to Berkovits. The low frequency roll-off point adjustment is achieved by changing the time constant of the high pass filter between the preamplifier and the main amplifier by inserting a fixed resistance in parallel with the filter resistance. The upper frequency roll-off point is modified by inserting a capacitor as a filtering element. Both of these adjustments are activated only at a predetermined level of noise to modify the roll-off point to a single preselected level and are maintained as long as the noise is above the predetermined level. Since only a single adjustment is available in the Berkovits patent, a considerable amount of instability, distortion and noise can be introduced until the threshold of the comparators are exceeded.

Thus, it can be seen that an improved electrocardiographic amplifier having a frequency response range which is a direct function of noise and can be continuously adjusted is needed.

SUMMARY OF THE INVENTION

An object of the present invention is to provide an improved electrocardiographic amplifier of whose frequency response can be adjusted by a digital signal.

Another object of the present invention is to provide a electrocardiographic amplifier whose low frequency response is continuously variable over a specific range.

Still another object of the present invention is to provide an electrocardiographic amplifier whose bandwidth is adjustable over wide ranges as a function of the noise detected by a microcomputer.

These and other objects are obtained in an electrocardiographic amplifier with low frequency roll-off control by providing an integrator in a feedback loop between the input and the output of the electrocardiographic amplifier and a switch in series therewith and a detector to detect the low frequency noise and vary the duty cycle of the switch using a digital signal to effectively adjust the time constant of the integrator and thereby the low frequency roll-off point. The selected duty cycle and, consequently, the 3 dB low frequency roll-off point can be a function of the detected noise. For high frequency noise, a capacitor and switch in series are provided in parallel with a feedback resistor of the electrocardiographic amplifier and a digital signal activates the switch to insert the capacitor to change the high frequency roll-off point down to a lower frequency.

Other objects, advantages and novel features of the present invention will become apparent from the following detailed description of the invention when considered in conjunction with the accompanying drawings.

DESCRIPTION OF THE PREFERRED EMBODIMENTS

Figure 1:
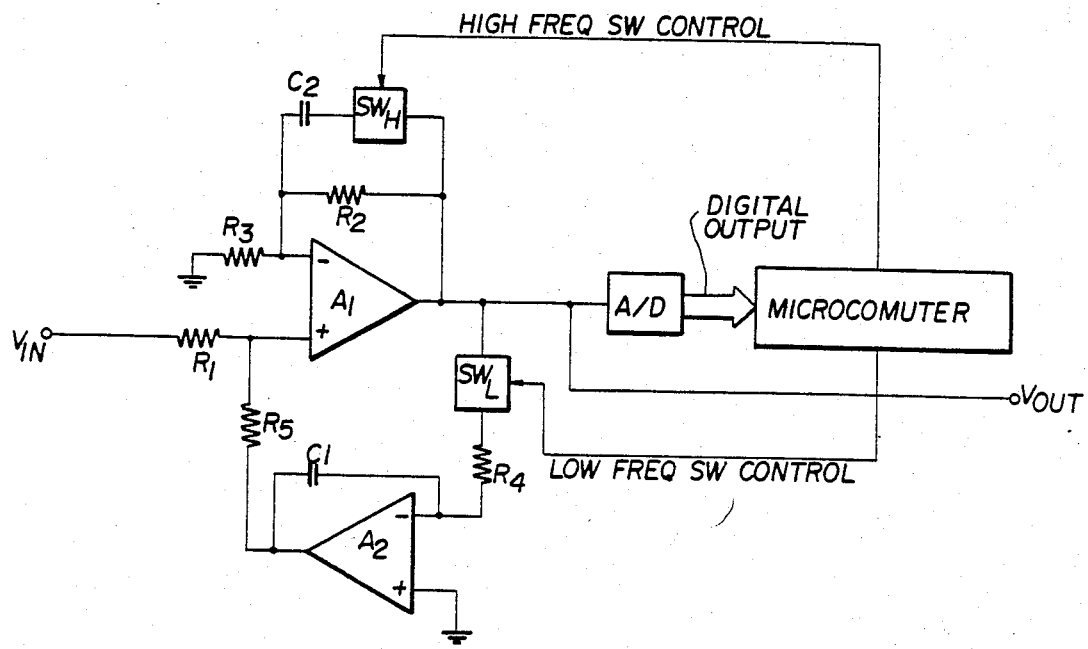
FIG. 1 is a block diagram schematic of n electrocardiographic amplifier incorporating the principles of the present invention.

An electrocardiographic amplifier is illustrated in FIG. 1 as including an input port $V_{IN}$ connected to the positive terminal of a first operation amplifier A1 through a series input resistance R1. The output of the operational amplifier is provided an output port as $V_{OUT}$ as an analog signal. A feedback resistor R2 connects the output of the operational amplifier A1 and its negative or inverting input port and a second resistor R3 connects the inverting or negative port to ground.

Connected between the output and the positive input of the first operational amplifier A1 is a low frequency roll-off adjustment circuit. This includes a low frequency switch $SW_L$, a resistor R4, a second operational amplifier A2 having a capacitor C1 in its feedback and a resistor R5. The second operational amplifier A2, its feedback capacitor C1 and resistor R4 form the integrator. The low frequency switch $SW_L$ determines how long the integrator is in the feedback loop and, thus, adjust the effective time constant of the integrator, as will be explained more fully below. This adjusts the low frequency roll-off point of amplifier A1.

A capacitor C2 is connected in series with a high frequency switch $SW_H$ both of which are in parallel with the feedback resistor R2 between the output and the negative input of the operation amplifier A1. The high frequency switch $SW_H$ determines when the capacitor C2 is in the feedback loop to adjust the high frequency roll-off point.

Connected to the output of the operational amplifier A1 is a noise detection and frequency bandwidth control system which includes an analog-to-digital converter and a microcomputer. The analog output of the amplifier is converted to a digital signal which is further processed by the microcomputer to detect low and high frequency noise. Once a high frequency noise has been detected, the microcomputer sends a digital high frequency switch control signal to $SW_H$ to add the capacitor C2 to the feedback circuit and thereby lower the high frequency roll-off point. Once a low frequency noise has been detected, the microcomputer sends a digital low frequency switch control signal to $SW_L$ whose duty cycle determines the effective time constant of the integrator and thereby raise the low frequency roll-off point.

Figure 2:
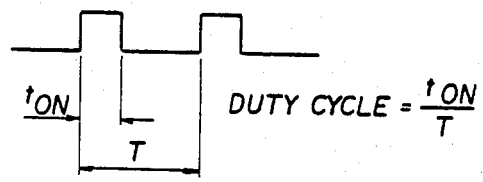
FIG. 2 is a graph of a signal used to control the low frequency switch of FIG. 1.

The integrator including resistor R4, capacitor C1 and the second operational amplifier A2 have a time constant substantially less than the minimum lower frequency roll-off point. The microcomputer detects the low frequency noise and increases the on-time of the low frequency switch $SW_L$ to lower the time constant of the integrator. As illustrated in FIG. 2, the time-on $t_{ON}$ relative to the complete time T of the pulses from the microcomputer defines the duty cycle D. The total time T represents the time constant of the integrator as determined by R4 and C1. Thus, it can be seen, that the time constant of the integrator may be varied over a wide range in values and is not limited merely to inserting or removing the integrator. Thus, the overall response of amplifier A1 can be tailored to the specific frequency of noise versus merely raising the lower frequency roll-off point.

Figure 3:
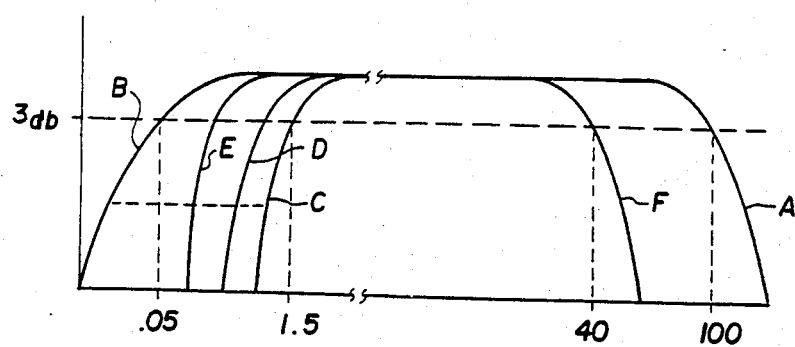
FIG. 3 is a typical graph of gain characteristics of the amplifier of FIG. 1.

The lower 3 dB roll-off point is 0.05 Hz when the integrator is in the feedback loop for the least amount of time as illustrated by curve B and the upper 3 dB roll-off point is 100 Hz as illustrated by curve A in FIG. 3. By increasing the duty cycle of the switch $SW_L$, the lower frequency 3 dB roll-off point may be raised from 0.05 Hz to 1.5 Hz as illustrated by curve C or any value therebetween, two of which are illustrated as D and E. By switching the integrator in and out a feedback loop versus modifying the input of the first operational amplifier A1, the present amplifier more quickly responds and has a shorter settling time than prior art methods and circuits.

The high frequency 3 dB roll-off point with switch $SW_H$ open is 100 Hz as illustrated by graph segment A. When high frequency noise is detected, switch $SW_H$ is closed to connect the capacitor C2 in parallel with the feedback resistor R2 to reduce the high frequency 3 dB roll-off point to 40 Hz as illustrated by graph segment F. Since the high frequency noise is generally in the 50 cycle or above range, and the amount of information lost by lowering the 3 dB point from 100 Hz to 40 Hz is not critical, only a single adjustment is illustrated in FIG. 1. If preferred, a plurality of parallel capacitors may be provided and with plural switches to select which capacitor will be connected in parallel with the feedback resistor R2.

Although a software implementation is described for the noise detector and switch control signals, since they are present in the newer electrocardiographic monitoring equipment, a hardware implementation is also possible. By using a microcomputer, more sophisticated noise detection techniques can be used. This increases the accuracy and speed of the low frequency adjustment and, thus, more of the analog signal is present for analysis.

From the preceding description of the preferred embodiments, it is evident that the objects of the invention are attained and although the invention has been described and illustrated in detail, it is to be clearly understood that the same is by way of illustration and example only and is not to be taken by way of limitation. The spirit and scope of the present invention are to be limited only the terms of the appended claims.

What is claimed is:

1. In an electrocardiographic amplifier including amplifying means, detecting means for detecting low frequency noise above a predetermined magnitude, and gain adjusting means responsive to said detecting means for adjusting the low frequency portion of said amplifying means gain by a fixed magnitude to control said noise, the improvement comprising:

said detecting means detects a plurality of low frequency noises and provides one of a plurality of adjustment signals having a duty cycle as a function of the detected low frequency noise; and said adjusting means adjusts said low frequency portion of said amplifying means gains to one of a plurality of magnitudes as a function of said adjustment signals, and includes an integrated means connected between the output and the input of said amplifying means in a feedback path and a switch means in series with said integrating means for enabling or disabling said feedback path in response to said adjustment signal to adjust the time constant of said grating means.

2. An electrocardiographic amplifier according to claim 1 including a detecting means for detecting high frequency noise above a predetermined magnitude, and adjusting means responsive to said high frequency detecting means for lowering the high frequency portion of said amplifying means to control said high frequency noise.

3. An electrocardiographic amplifier according to claim 2, wherein said amplifying means includes a resistor in a inverting feedback path, and said high frequency adjusting means includes a capacitor in parallel with said feedback resistor and a switch means in series with said capacitor and responsive to said high frequency detecting means for inserting and removing said capacitor from said feedback path.

4. An electrocardiographic amplifier comprising:
an operational amplifier having an input and an output;
an integrator connected in a feedback path between said input and output;
a switch in series with said integrator in said feedback path; and
detecting means responsive to low frequency noises in the signal on said output for controlling the duty cycle of said switch to adjust the time constant of said integrator as a function of the low frequency noise to adjust the low frequency roll-off of said amplifier.

5. An electrocardiographic amplifier according to claim 4, wherein said integrator includes an operational amplifier with a series resistance on its input and a capacitor connected between its output and its input.

6. An electrocardiographic amplifier according to claim 4 including a detecting means for detecting high frequency noise above a predetermined magnitude, and adjusting means responsive to said high frequency detecting means for lowering the high frequency portion of said amplifying means to control said high frequency noise.

7. An electrocardiographic amplifier according to claim 6 wherein said amplifying means includes a resistor in a inverting feedback path, and said high frequency adjusting means includes a capacitor in parallel with said feedback resistor and a switch means in series with said capacitor and responsive to said high frequency detecting means for inserting and removing said capacitor from said feedback path.

* * * * *